United States Patent
McCloskey et al.

(10) Patent No.: US 10,910,105 B2
(45) Date of Patent: Feb. 2, 2021

(54) MONITORING THE USE OF LANGUAGE OF A PATIENT FOR IDENTIFYING POTENTIAL SPEECH AND RELATED NEUROLOGICAL DISORDERS

(71) Applicant: International Business Machines Corporation, Armonk, NY (US)

(72) Inventors: Daniel J. McCloskey, Dublin (IE); Harshita Nersu, Dublin (IE)

(73) Assignee: International Business Machines Corporation, Armonk, NY (US)

(*) Notice: Subject to any disclaimer, the term of this patent is extended or adjusted under 35 U.S.C. 154(b) by 393 days.

(21) Appl. No.: 15/609,171

(22) Filed: May 31, 2017

(65) Prior Publication Data
US 2018/0349560 A1    Dec. 6, 2018

(51) Int. Cl.
| | |
|---|---|
| *G16H 40/63* | (2018.01) |
| *G09B 19/00* | (2006.01) |
| *G10L 25/66* | (2013.01) |
| *A61B 5/00* | (2006.01) |
| *A61B 5/16* | (2006.01) |

(Continued)

(52) U.S. Cl.
CPC .......... *G16H 40/63* (2018.01); *A61B 5/0022* (2013.01); *A61B 5/16* (2013.01); *A61B 5/4803* (2013.01); *G06F 40/30* (2020.01); *G10L 15/02* (2013.01); *G10L 15/1815* (2013.01); *G10L 15/19* (2013.01); *G10L 15/22* (2013.01); *G10L 25/66* (2013.01); *G10L 25/90* (2013.01); *G16H 10/60* (2018.01); *A61B 5/48* (2013.01); *A61B 5/741* (2013.01); *G09B 19/00* (2013.01); *G16H 50/30* (2018.01)

(58) Field of Classification Search
None
See application file for complete search history.

(56) References Cited

U.S. PATENT DOCUMENTS

2011/0123967 A1* 5/2011 Perronnin ............... G09B 7/02
434/178
2012/0265024 A1  10/2012 Shrivastav et al.
(Continued)

OTHER PUBLICATIONS

PCT/EP2017/082861, ISR and Written Opinion, dated Mar. 9, 2018, 15 pages.
(Continued)

*Primary Examiner* — James B Hull
(74) *Attorney, Agent, or Firm* — Schmeiser, Olsen & Watts, LLP; William Hartwell

(57) ABSTRACT

A method and associated computer system and computer program product for monitoring the use of language of a patient that may enable the identification, analysis and reporting on of the natural progression of various neurological or speech disorders, is provided. The method includes obtaining a verbal response of the patient to a stimulus, converting the verbal response into text and the generating of verbal and textual response data by analyzing the verbal response and response text, respectively. A response vector may be formed base on the verbal and textual response data, which may then be used to determine a reply to the patient. Improved accuracy and consistency of monitoring the use of language associated with neurological and speech disorders is achieved, leading to a greater rate of success in the treatment of these conditions.

16 Claims, 5 Drawing Sheets

(51) Int. Cl.
*G06F 40/30* (2020.01)
*G16H 10/60* (2018.01)
*G10L 15/02* (2006.01)
*G10L 15/18* (2013.01)
*G10L 15/19* (2013.01)
*G10L 15/22* (2006.01)
*G10L 25/90* (2013.01)
*G16H 50/30* (2018.01)

(56) References Cited

U.S. PATENT DOCUMENTS

| | | | |
|---|---|---|---|
| 2012/0311461 A1* | 12/2012 | Granof | G06Q 10/00 715/753 |
| 2014/0038160 A1 | 2/2014 | Shani et al. | |
| 2015/0046357 A1* | 2/2015 | Danson | G06Q 10/1053 705/321 |
| 2015/0118661 A1 | 4/2015 | Haruta et al. | |
| 2016/0171901 A1* | 6/2016 | Beketayev | G09B 7/02 434/362 |
| 2016/0246947 A1* | 8/2016 | Yao | G16H 10/20 |
| 2016/0314784 A1 | 10/2016 | Kleppe et al. | |
| 2017/0019775 A1* | 1/2017 | Tavares | H04W 4/12 |
| 2017/0084295 A1 | 3/2017 | Tsiartas et al. | |
| 2018/0232752 A1* | 8/2018 | BaderEddin | G06Q 30/0203 |
| 2018/0322961 A1* | 11/2018 | Kim | A61B 5/1123 |

OTHER PUBLICATIONS

Examination Report, Application No. 17 822 625.4-1207, dated Jul. 22, 2020, 4 pages.

* cited by examiner

MONITORING THE USE OF LANGUAGE OF A PATIENT FOR IDENTIFYING POTENTIAL SPEECH AND RELATED NEUROLOGICAL DISORDERS

TECHNICAL FIELD

The present invention relates to the use of language of a patient, and more particularly to methods for monitoring the use of language for a patient based on data collected from the patient, which may be useful for identifying potential speech or neurological disorders.

BACKGROUND

Early intervention has been identified as a key factor in the successful treatment of neurological and speech disorders, such as Autism Spectrum Disorders (ASD) and Dyspraxia.

SUMMARY

An aspect of this invention relates to a method, and associated computer system and computer program product for monitoring a use of language of a patient. A processor of a computing system obtains a verbal response of the patient to a stimulus. The verbal response is converted into a response text. Verbal response data is generated by analyzing the verbal response. Textual response data is generated by analyzing the response text. A response vector is formed based on the verbal response data and the textual response data. A reply to the patient is determined based on the response vector.

DETAILED DESCRIPTION

Figure 1:
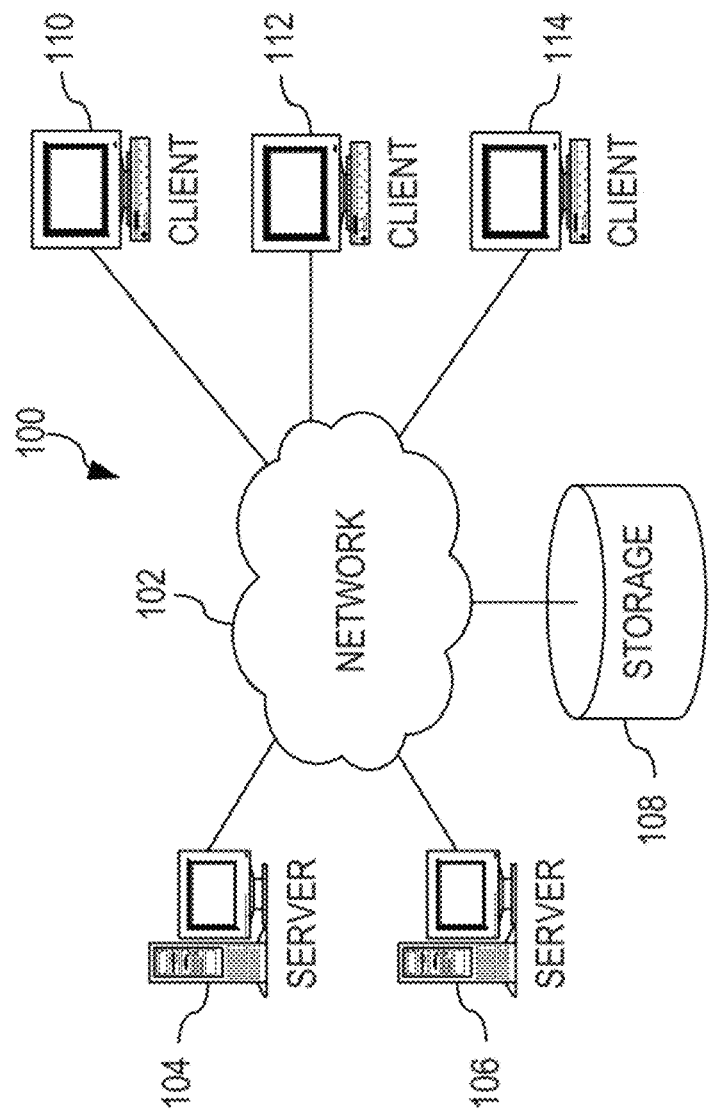
FIG. 1 depicts a pictorial representation of an example distributed data processing system, in accordance with embodiments of the present invention.

Current limitations, such as healthcare system costs, capacity and policies, can cause severe delays in a detection of a disorder; leading to a corresponding, and often significant, impact on the prognosis and future quality of life of the patient. Moreover, intervention strategies are not infallible and are known to achieve inconsistent accuracy, which is often dependent on the capabilities and resources of individual practitioners.

Accordingly, a need exists for systems and methods for monitoring the use and acquisition of language of a patient in order to provide consistently accurate diagnoses of neurological and speech disorders at an early stage in the condition's development.

Embodiments of the present invention relate to a method for monitoring the use of language of a patient that may enable the identification, analysis and reporting of the natural progression of various neurological or speech disorders. Embodiments of the method may include obtaining a verbal response of the patient to a stimulus, converting the verbal response into text, and generating verbal and textual response data by analyzing the verbal response and response text, respectively.

A response vector may be formed based on the verbal and textual response data, which may then be used to determine a reply to the patient. A further use of the response vector may be to assign a classification to the patient. Proposed embodiments may thus provide improved accuracy and consistency of monitoring the use of language associated with neurological and speech disorders, leading to a greater rate of success in the treatment of these conditions.

Embodiments of the present invention further provides a computer program product including computer program code for implementing the proposed analysis concepts when executed on a processor.

Embodiments of the present invention further provides a system (such as a processing device and/or network component) configured to execute this computer program code.

According to an embodiment of the present invention, a computer-implemented method for monitoring the use of language of a patient, the method comprising: obtaining a verbal response of the patient to stimulus; converting the verbal response into a response text; generating verbal response data by analyzing the verbal response; generating textual data by analyzing the response text; forming a response vector based on the verbal response data and the textual response data; and determining a reply to the patient based on the response vector.

Proposed is a concept of analyzing the verbal response of a patient to a stimulus, wherein the analysis is performed on both the audio profile of the verbal response and the converted response text. The data from these analyses is used to build a profile of the patient's response in the form of a response vector, which forms the basis of a reply to the patient. The reply may be used as a further stimulus for gathering additional verbal responses from the patient. The additional verbal responses may then be used to update the response vector according to each new response.

Put another way, proposed may be a concept of establishing a continuous dialogue with a patient, wherein the patient's responses may be analyzed, in audio and text form, to monitor the use of language of the patient, which may be indicative of a neurological or speech disorder.

In an exemplary embodiment, the stimulus provided to the patient may comprise at least one of: an audible component; a visual component; a hepatic component; a taste component; a smell component; a text-based component; a question; a picture; and a video.

According to an aspect of this embodiment, the patient may be encouraged to provide a verbal response through the posing of simple questions. The answers to these questions may have predetermined responses, or the answers may vary depending on the context of the conversation. In the case of predetermined, or expected, answers being known, it may be possible to quickly analyze the patient's verbal response by comparing the patient's verbal response to the known answer.

Patients suffering from a neurological or speech disorder are often times extremely visually orientated. In other words, patients suffering from a neurological or speech disorder often respond more readily to visual learning techniques. By providing a stimulus that comprises a visual component, a patient may respond in a more positive manner to the stimulus, or reply to the patient, and may be more willing to provide a verbal response. This in turn may aid the diagnostic procedure as there will be more verbal data supplied by the patient, which may be particularly relevant to the case where the patient is a child.

As an example, a child may be provided with a stimulus that comprises a picture of a mouse and the question, "What is this?" The child may then provide a response which may then be recorded and analyzed. In this case, the analysis may include comparing the child's response to the content of the picture in order to check whether the child's response matches the content of the picture. Here, the expected response may be, "It is a mouse", or a similar statement indicating a mouse being present.

In some embodiments, the verbal response data may be generated by analyzing a phonetic component of the verbal response, wherein the phonetic component may comprise a pitch level.

In this way, it may be possible to identify multiple speech disorders, for example, a stutter may be detected if there is a stammer cadence present in the verbal response. Returning to the previous example, a response of the form, "I-i-i-it is a m-m-m-mouse", may provide an indication that the child has a stutter. The indication that the child has a stutter y form part of the verbal response data to be used in the formation of the response vector.

Whilst the above example deals purely with a speech disorder, it may also be useful to include these aspects in the analysis of language acquisition, relating to neurological disorders, as there may be various key indicators within the phonetic components of the response. For example, irregular pauses between words may indicate that a patient is struggling to acquire the correct word to respond to the provided stimulus. In this case, the child's response may take the form of, "It is a . . . mouse", where the regular cadence of the child's speech has been interrupted by an irregular pause before the word 'mouse'. The irregular pause may serve as an indication that the child is struggling to acquire the word 'mouse' from the child's vocabulary.

The child's responses to the stimulus may further indicate that a patient is struggling to form the correct response to the provided stimulus by analyzing the pitch of the verbal response. The pitch of the verbal response may indicate that a patient is unsure of the patient's response or that the patient is struggling to acquire the correct words and/or sentence structure.

In some embodiments, the textual response data may be generated by analyzing at least one of a semantic component and a grammatical component of the response text.

Analyzing the at least one of a semantic component and a grammatical component of the response text may allow the meaning of the words within the verbal response to be analyzed and compared to the provided stimulus, meaning that the cognitive process behind forming the response may be analyzed in more depth and a more accurate patient profile produced. Returning to the example of the mouse, the child may provide a response of the form, "It is a bird", without any audible irregularities present. In this case, a purely audio based analysis may not detect that the semantic content of the response does not match the stimulus; however, by analyzing the semantics of the response, it may be possible to detect that the child's response is incorrect. The child's incorrect response may be used as a factor in the patient classification process according to embodiments of the method. In a further example, the child may provide a response of the form, "It is chased by a cat", where the specific word 'mouse' is not present, but a common connection to a mouse has been made. Through understanding the meaning of the child's response, it may be possible to assess a level of correctness, which may in turn lead to a more accurate condition profile.

By further analyzing the grammatical content of the verbal response, it may be possible to produce a more accurate classification of the neurological or speech disorder that the patient belongs to. For example, the patient may use the incorrect pronoun in a sentence and give a response of the form, "I am a mouse", in the case of the mouse example. In other words, the response may be provided with no audible discrepancies and the correct subject, the 'mouse', may have been identified; however, the structure of the response remains incorrect. By identifying this mistake, it may be possible to provide a reply to the patient, such as "It is a mouse, isn't it?", that attempts to correct the mistake and provide the patient with a further stimulus that encourages the patient to try again. The textual analysis may reveal key cognitive identifiers for neurological disorder that are not present in the audio profile of the response.

In an exemplary embodiment, the method may further comprise: obtaining a motor response of the patient to the stimulus; generating motor response data by analyzing the motor response; forming a motor response vector based on the motor response data; and forming an overall response vector based on the motor response vector and the response vector.

In other words, embodiments of the method may also take into account the movement of the patient, such as eye movement, facial expression, posture and the like, in order to gain additional information for use in the generation of a response to the patient.

Put another way, by including additional factors in the analysis of the patient's response, a more accurate neurological profile may be constructed for the patient.

In some embodiments, the step of determining a reply to the patient may comprise: identifying a plurality of candidate conditions by analyzing the response vector; determining a confidence score for each candidate condition based on the contents of the response vector; identifying a potential reply to the verbal response based on the confidence scores; and contextualizing the potential reply based on at least one of the previous replies to the patient, the previous recorded verbal responses and the stimulus.

The response vector may include a variety of different metrics by which the patient's response is analyzed, for example, the variation in pause length between words, the sentence length, the number of grammatical errors and the like. The performance of the patient with respect to each of these metrics may allow the response vector to be classified as matching a certain condition. As conditions are classified using idealized data, the patient response may be classified into a plurality of different conditions.

By assigning each matching condition a confidence score, wherein the confidence score depends on the strength of the match, the closest matching condition profile to the patient's response may be identified.

In some cases, there may be multiple replies that could be supplied to the patient. By determining the most appropriate reply to the verbal response of the patient, it may be possible to increase the efficiency of the system. Returning once again to the example of the mouse, the child may provide the response, "I am a mouse", and so the analysis would reveal that the incorrect pronoun has been used by the patient. Based on this analysis, an equivalent case with a different patient, wherein the patient also supplied a similar response, may be used to select an appropriate response.

However, it may be the case that a different stimulus is used, for example, a picture of a cat. This may lead to the selected reply to the patient being of the form, "It is a cat, isn't it?" Clearly, the child's response is incorrect and may lead to confusion of the patient. In this scenario, the ply mazy be contextualized in order to align the reply's content with the current patient interaction. The subject of the potential response, a cat, may be compared to the subject of the current patient interaction, a mouse. If the subject of the potential response and the subject of the current patient interaction are found to not match, the subject of the potential response may be replaced with the subject on the current interaction, which may lead to the reply supplied to the patient taking the correct form of, "It is a mouse, isn't it?"

In an exemplary embodiment, a candidate condition may be identified as a primary condition if the candidate condition's determined confidence score is above a predetermined value.

Put another way, if the confidence level of a candidate condition is above a predetermined level, the patient is diagnosed with that condition. The confidence level may also be provided to the patient or care giver.

In some embodiments, the step of identifying the potential reply may comprise; comparing the verbal response to existing clinical knowledge; comparing the verbal response to prior responses given by the patient; comparing the verbal response to documented language discussions; or any combination thereof; and identifying a potential reply to the patient based on the comparison.

Such embodiments may allow the verbal response of the patient to be compared to existing clinical knowledge, such as various standardized test results across a plurality of conditions. This knowledge may be accessed before any patient interactions begin, allowing key condition indicators to be recognized quickly and efficiently once the process begins, meaning that the identified potential reply may include standardized components designed to reveal certain conditions. In addition, the verbal response may be compared to previous verbal responses given by the patient. In the case of the incorrect pronoun example, the first verbal response given was, "I am a mouse", to which the reply may have been "It is a mouse, isn't it?" The second response supplied by the patient may then be of the form, "It is a mouse", which may then be compared to the first verbal response. Through this comparison it may be possible to see that the patient has improved, in which case the conversation may be marked as successful.

Further still, the verbal response may be compared to documented language discussions, such as those found in scientific research journals, therapeutic advice guides, online discussion forums and the like. Through a combination of these comparisons, it may be possible to increase the efficiency of building the complex neurological and speech profile of a patient by comparing the patient's verbal profile to known examples.

In various embodiments, the method may further comprise: providing the reply as a further stimulus to the patient; obtaining a further verbal response of the patient to the further stimulus; converting the further verbal response into a further response text; generating further verbal response data by analyzing the further verbal response; generating further textual response data by analyzing the further response text; forming a further response vector based on the further verbal response data and the further textual response data; determining a further reply to the patient based on the further response vector.

In this embodiment, the method may be repeated in order to gather more verbal data from the patient. In this case, the reply given to the patient is determined based on the candidate conditions and the verbal response data in order to provide the most appropriate stimulus to the patient.

In other words, the method may be repeated in order to form a continuous dialogue with the patient in order to gather a large amount of verbal data, allowing for a more accurate monitoring of the patient's use of language.

According to further embodiments of the invention, there is herein provided a computer program product for monitoring the use and acquisition of language of a patient, the computer program product comprising a computer readable storage medium having program instructions embodied therewith, the program instructions executable by a processing unit to cause the processing unit to perform a method comprising: obtaining a verbal response of the patient to a stimulus; converting the verbal response into a response text; generating verbal response data by analyzing the verbal response; generating textual response data by analyzing the response text; forming a response vector based on the verbal response data and the textual response data; determining a reply to the patient based on the response vector.

According to yet another aspect, there is provided a processing system comprising at least one processor and the computer program product according to one or more embodiments, wherein the at least one processor is configured to execute the computer program code of the computer program product.

The processing system may be configured to act as language use and acquisition monitoring component situated between a care giver and a patient. The processing system may be configured to implement a part of an off-premise platform, such as a cloud-based system or server.

Thus, embodiments of a system may analyze the verbal response of a patient, in audio and text form, and diagnose the condition of the patient based on the result of the analysis.

Thus, according to further embodiments of the invention, there is also herein provided a system for monitoring the use and acquisition of language of a patient, the system comprising: a device configured to obtain a verbal response of the patient to a stimulus; a processing unit configured to convert the verbal response into a response text; a first data generation unit configured to generate verbal response data by analyzing the verbal response; a second data generation unit configured to generate textual response data by analyzing the response text; a data processing unit configured to form a response vector based on the verbal response data and the textual response data; and a reply generation unit configured to determine a reply to the patient based on the response vector.

The stimulus may comprise at least one of, an audible component, a visual component, a text-based component, a question, a picture and a video.

The first data generation unit may be further configured to generate verbal response data by analyzing a phonetic component of the verbal response, wherein the phonetic component may comprise a pitch level.

In an exemplary embodiment, the second data generation unit may be further configured to generate textual response data by analyzing at least one of a semantic component and a grammatical component of the response text.

In another embodiment, the system may further comprise: a second device configured to obtain the motor response of the patient to the stimulus; a third data generation unit configured to generate motor response data by analyzing the motor response; a second data processing unit configured to form a motor response vector based on the motor response data; and a third data processing unit configured to form an overall response vector based on the motor response vector and the response vector.

The reply generation unit may be further configured to: identify a plurality of candidate conditions by analyzing the response vector; determine a confidence score for each candidate condition based on the contents of the response vector; identify a potential reply to the verbal response based on the confidence scores; and contextualize the potential reply based on at least one of the previous replies to the patient, the previous recorded verbal responses and the stimulus.

In an exemplary embodiment, the reply generation unit may be further configured to identify a candidate condition as a primary condition if the candidate condition's determined confidence score is above a predetermined value.

In various embodiments, the reply generation unit may, for the process of identifying a potential reply, be configured to; compare the verbal response to existing clinical knowledge; compare the verbal response to prior responses given by the patient; compare the verbal response to documented language discussions; or any combination thereof; and identify a potential reply to the patient based on the comparison.

In some embodiments, the system may further comprise: a user interface configured to provide the reply as a further stimulus to the patient; a device configured to obtain a further verbal response of the patient to the further stimulus; a processing unit configured to convert the further verbal response into a further response text; a first data generation unit configured to generate further verbal response data by analyzing the further verbal response; a second data generation unit configured to generate further textual response data by analyzing the further response text; a data processing unit configured to form a further response vector based on the further verbal response data and the further textual response data; a reply generation unit configured to determine a further reply to the patient based on the further response vector.

Furthermore, a (processing) system may be a single device or a collection of distributed devices that are adapted to execute one or more embodiments of the methods of the present invention. For instance, a system may be a personal computer (PC), a server or a collection of PCs and/or servers connected via a network such as a local area network, the Internet and so on to cooperatively execute at least one embodiment of the methods of the present invention.

The illustrative embodiments relate to a computer implemented method for monitoring the use of language of a patient. The concept may include: obtaining a verbal response of the patient to a stimulus; converting the verbal response into a response text; generating verbal response data by analyzing the verbal response; generating textual response data by analyzing the response text; forming a response vector based on the verbal response data and the textual response data; and determining a reply to the patient based on the response vector.

Put another way, embodiments of the present invention may include a language monitoring method, wherein a reply to the patient is generated based on the response of the patient to a stimulus. The verbal and textual content of the patient's response may be analyzed in order to generate the most appropriate response. The generated response may form a new stimulus in order to establish a conversation with the patient, wherein each response given by the patient may be further analyzed.

Embodiments may enable a data processing system to obtain a verbal response from a patient to a stimulus, convert the verbal response into a response text, generate verbal response data by analyzing the verbal response, generate textual response data by analyzing the response text, form a response vector based on the verbal response data and the textual response data and determined a reply to the patient based on the response vector. Further embodiments may also obtain information relating to a motor response of the patient to the stimulus. Possible stimuli may include an audible component, a visual component, a hepatic component, a taste component, a smell component, a text-based component, a question, a picture and a video.

In particular, embodiments of the present invention may include a computer implemented method to initiate a conversation with a patient, wherein each reply to the patient may act as a new stimulus, which may allow for multiple patient responses to be analyzed, which may allow for a detailed profile to be built of the cognitive condition of the patient.

Modifications and additional steps to a traditional language monitoring implementation may also be provided to enhance the value and utility of embodiments of the present invention.

Figure 2:
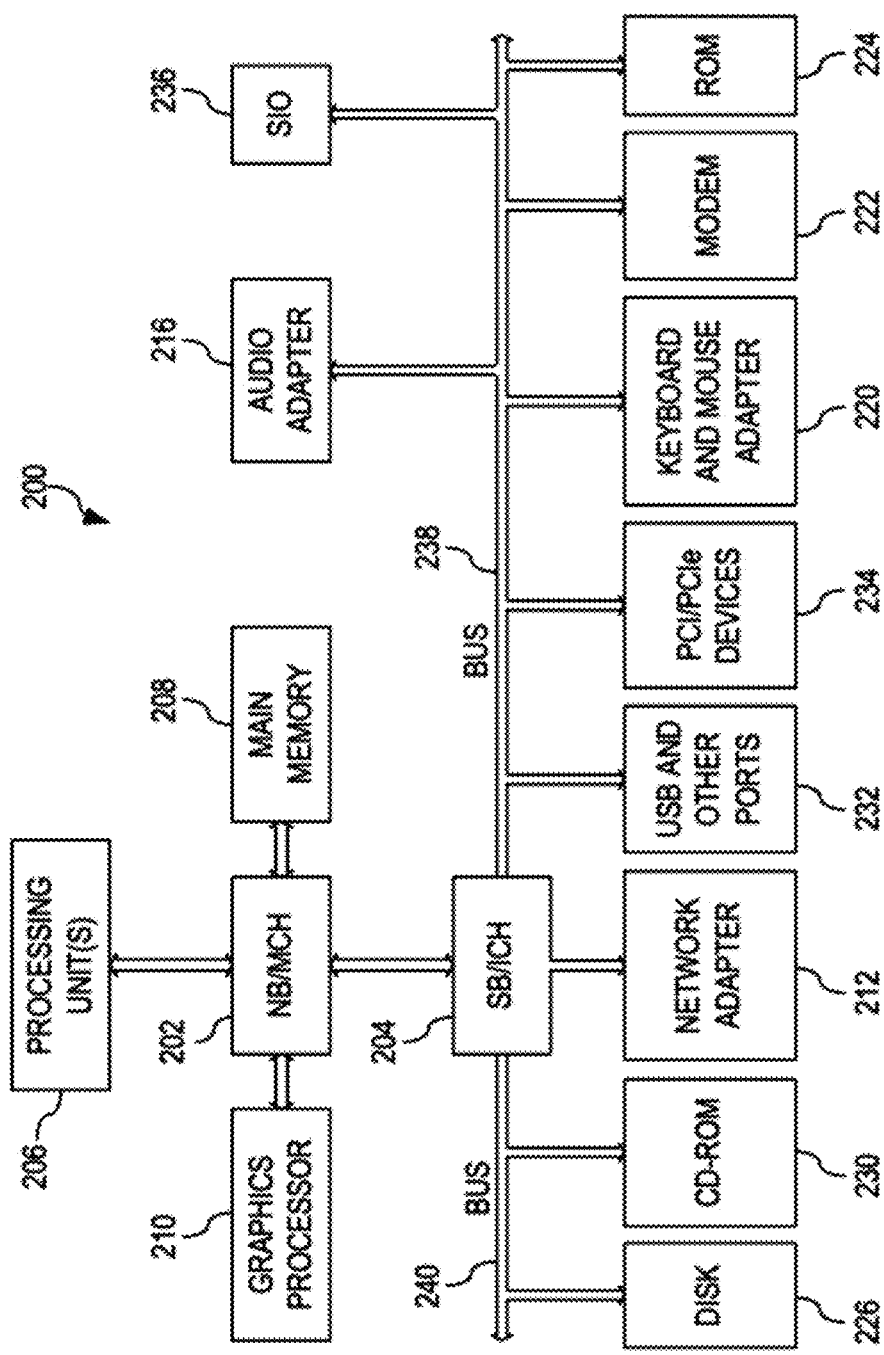
FIG. 2 is a block diagram of an example data processing system, in accordance with embodiments of the present invention.

Illustrative embodiments may be utilized in many different types of data processing environments. In order to provide a context for the description of elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system, in accordance with embodiments of the present invention. Distributed data processing system 100 may include a network of computers in which aspects of the illustrative embodiments may be implemented. The distributed processing system 100 contains at least one network 102, which is the medium used to provide communication links between various devices and computers connected together within distributed data processing system 100. The network 102 may include connections, such as wire, wireless communication links, or fiber optic cables.

In the depicted example, a first server 104 and a second server 106 are connected to the network 102 along with a storage unit 108. In addition, clients 110, 112, and 114 are also connected to the network 102. The clients 110, 112, and 114 may be, for example, personal computers, network computers, or the like. In the depicted example, the first server 104 provides data, such as boot files, operating system images, and applications to the clients 110, 112, and 114. Clients 110, 112, and 114 are clients to the first server 104 in the depicted example. The distributed processing system 100 may include additional servers, clients, and other devices not shown.

In the depicted example, the distributed processing system 100 is the Internet with the network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

FIG. 2 is a block diagram of an example data processing system, in accordance with embodiments of the present invention. The data processing system 200 is an example of a computer, such as client 110 in FIG. 1, in which computer usable code or instructions implementing the processes for illustrative embodiments of the present invention may be located.

In the depicted example, the data processing system 200 employs a hub architecture including a north bridge and memory controller hub (NB/MCH) 202 and a south bridge and input/output (I/O) controller hub (SB/ICH) 204. A processing unit 206, a main memory 208, and a graphics processor 210 are connected to NB/MCH 202. The graphics processor 210 may be connected to the NB/MCH 202 through an accelerated graphics port (AGP).

In the depicted example, a local area network (LAN) adapter 212 connects to SB/ICH 204. An audio adapter 216, a keyboard and a mouse adapter 220, a modem 222, a read only memory (ROM) 224, a hard disk drive (HDD) 226, a CD-ROM drive 230, a universal serial bus (USB) ports and other communication ports 232, and PCI/PCIe devices 234 connect to the SB/ICH 204 through first bus 238 and second bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

The HDD 226 and CD-ROM drive 230 connect to the SB/ICH 204 through second bus 240. The HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on the processing unit 206. The operating system coordinates and provides control of various components within the data processing system 200 in FIG. 2. As a client, the operating system may be a commercially available operating system. An object-oriented programming system, such as the Java® programming system, may run in conjunction with the operating system and provides calls to the operating system from Java® programs or applications executing on data processing system 200.

As a server, data processing system 200 may be, for example, an IBM® eServer™ System P® computer system, running the Advanced Interactive Executive (AIX®) operating system or the LINUX® operating system. The data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. Similarly, one or data structures according to an embodiment may be adapted to be stored by the storage devices and/or the main memory 208.

The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as first bus 238 or second bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as the modem 222 or the network adapter 212 of FIG. 2, may include one or more devices used to transmit and receive data. A memory may be, for example, main memory 208, ROM 224, or a cache such as found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to multiprocessor/server systems, other than those illustrated, without departing from the scope of the proposed concepts.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, the data processing system 200 may be a portable computing device that is configured with flash memory to provide non-volatile memory for storing operating system files and/or user-generated data, for example. Thus, the data processing system 200 may essentially be any known or later-developed data processing system without architectural limitation.

Embodiments of the present invention may enhance a language monitoring (such as that depicted in FIG. 2) by providing for data relating to the cognitive function of a patient to be generated based on the analysis of a response of the patient to a stimulus.

Figure 3:
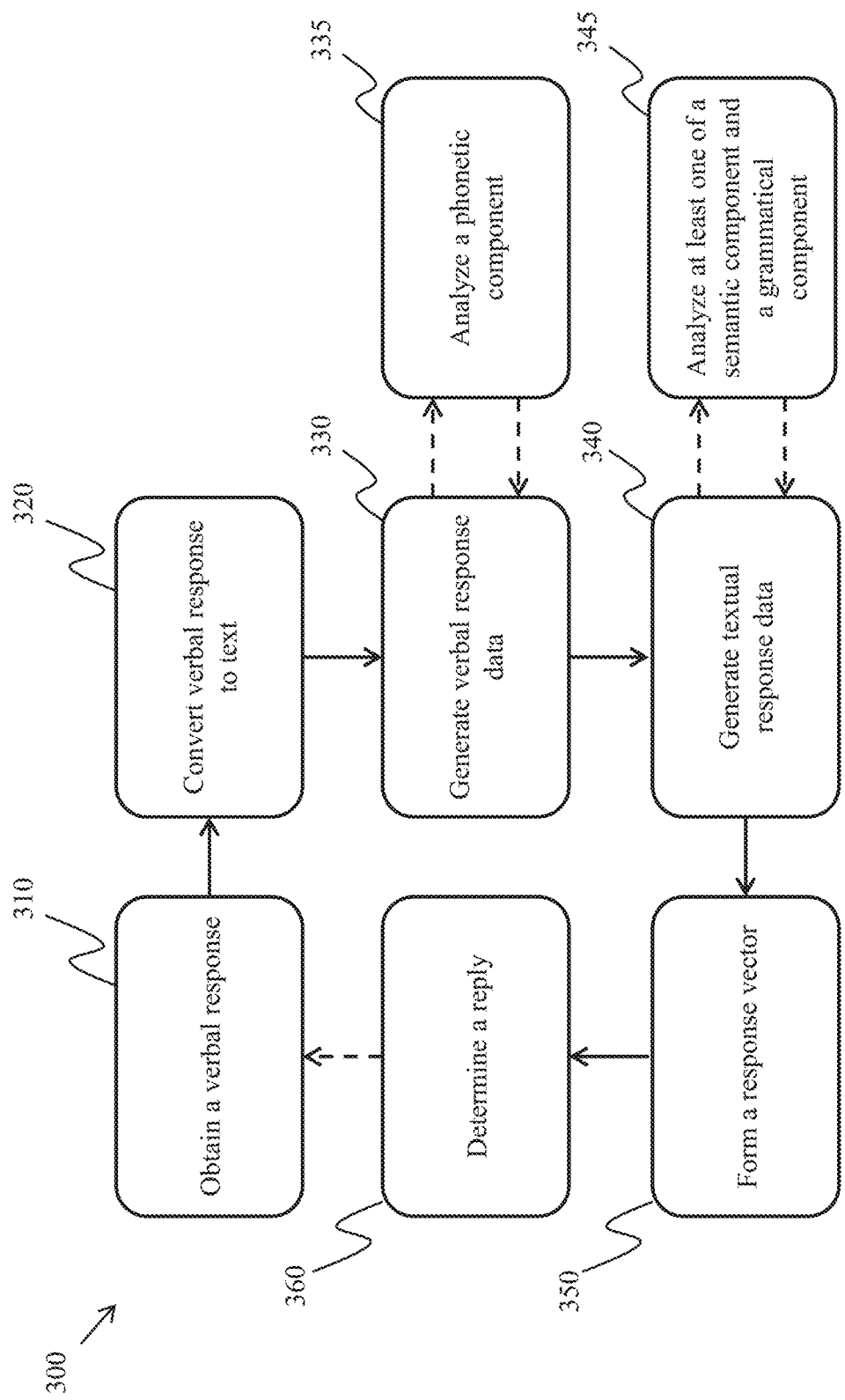
FIG. 3 depicts a flowchart of a method for monitoring the use of language of a patient, in accordance with embodiments of the present invention.

FIG. 3 depicts a flowchart of a method 300 for monitoring the use of language of a patient, in accordance with embodiments of the present invention. The process may begin in step 310, wherein a verbal response to a stimulus may be obtained from the patient.

Depending on the age and condition of the patient, different stimuli may have varying rates of success for encouraging a verbal response. For example, in the case that the patient is a child, a visual stimulus may have a greater chance of success in encouraging a verbal response from the child when compared to a text-based stimulus. In addition, it is often the case that patients with certain conditions may be extremely visually orientated. A visual stimulus may have a greater chance of success compared to an audible stimulus.

As a further example, a patient may suffer from a cognitive impairment or a brain injury, the nature of which dictates the most appropriate stimulus to use for the patient. The stimulus may comprise at least one of: an audible component; a visual component; a hepatic component; a taste component; a smell component; a text-based component; a question; a picture; and a video. The most appropriate combination of stimuli may be selected individually for the patient, based on the nature of the patient's condition.

In an exemplary embodiment, a standardized test may be used for the assessment of a specific condition of the patient, wherein the standardized test may make use of predetermined stimuli. In this way, it may be possible to obtain the response of different patients to the same stimuli, which in turn may allow for a comparison to be made between patient responses. Patients that provide similar responses may be classified as belonging to a group that share similar attributes.

In other words, by using a standardized set of stimuli, patient responses may be compared and grouped based on the associated response vectors formed from each response.

In step 320, the verbal response of the patient may be converted into text to form a textual response. The conversion of the verbal response into text may be performed by speech-to-text systems. The conversion of the verbal response into text may allow for in-depth linguistic analysis to be performed on the patient's response.

Put another way, the response of the patient to the stimulus may be stored in an audio format, which may then be converted to text. In this way, the patient's response may be stored in both audio and text-based format.

In step 330, verbal response data may be generated by analyzing the audible component of the patient's response. Analyzing the audible component of the patient's response may include analyzing a phonetic component of the patient's response, as in step 335.

By storing the patient's response in audio format, various prosodic and phonetic features of the patient's response may be analyzed in order to generate the verbal response data. These features may include: the pitch of the patient's voice; the cadence of the patient's response; the variance in the pause length between words; and the like. The analysis of features such as these may indicate various conditions associated with the patient, such as a stammer. Further, the cognitive function of a patient may be assessed through features, such as the pitch of the patient's voice or extended pauses between words that may indicate that a patient is struggling to acquire the correct word to use or to form the response into a full sentence.

Whilst the phonetic features may provide an indication of a condition of a patient, the verbal response data generated from the analysis of these phonetic features may be used to build an in-depth cognitive profile of the patient in the form of the response vector. In other words, the combination of the verbal response data with the textual response data may allow for cognitive conditions to be identified that may not have been readily apparent from the audio profile of the response alone.

In step 340, textual response data may be generated by analyzing the textual response obtained in step 320. The textual analysis may include analyzing at least one of a semantic component and a grammatical component of the response, as in step 345.

In an exemplary embodiment, the text may be broken down using Natural Language Processing, referred to as NLP, into word tokens. Breaking down the text into word tokens may be referred to as Tokenization. Further foundational linguistic analysis may include: identifying Part-of-Speech values for the words, known as POS Tagging; creating a dependency parse tree, referred to as Parsing; assigning semantic roles to terms and phrases in the utterance, referred to as SRL; identifying named entities; and resolving co-references, such as anaphora and cataphora, known as co-ref resolution.

Co-ref resolution may be applied across a conversation in order to assess whether anaphora, such as pronouns, used by the patient are in agreement with the subject of the patient response. In the case that a pronoun reference is not resolved within the context of the most recent patient response, previous responses may be checked in order to assess whether the use of the pronoun is correct within the context of the conversation as a whole.

By way of example, a patient response may be of the form, "John is bad, I don't like him." In this case, the pronoun, him, is correct in the context of this response. Alternatively, this may take the form of a conversation, wherein the first patient response may be, "John is bad", to which a reply to the patient may be, "Do you like John?" The patient may then respond to the reply to the patient by saying, "I don't like him." In this way, by taking the conversation as a whole, it may be seen that the pronoun used by the patient is correct; whereas, if the response, "I don't like him", were to be analyzed in isolation, the pronoun use may be incorrectly identified as being wrong.

Beyond these foundational linguistic features, higher level features may be generated. For example, in the case of language acquisition and Autism specific language progression, features such as: sentence and clause length; clausal complexity; scoring of vocabulary use; repetition of words; and broken agreement may be common.

By analyzing these features, it may be possible to directly assess the cognitive function of a patient in order to identify conditions that may not be readily apparent from the audio profile of the patient's response or the low level text-based features.

In step 350, a response vector may be formed based on both the verbal response data and the textual response data. The response vector may then be thought of as a multidimensional representation of the patient response, combining both speech specific and linguistic features gathered from the verbal response data and the textual response data respectively. The response vector may then be classified using various techniques. In one embodiment, machine learning classifiers such as Support Vector Machines, referred to as SVM, or a Recurrent Neural Network, known as RNN, may be used.

In step 360, a reply to the patient is determined based on the response vector. A method for determining a reply to the patient is further described in relation to FIG. 4.

In various embodiments, the reply generated in step 360 may be presented to the patient as a new stimulus so as to repeat the method and form a continuous dialogue with the patient. In this way, a greater amount of data may be obtained from the patient so as to enhance the accuracy of the response vector.

In some embodiments, the reply to the patient may attempt to correct a mistake identified in the patient's response. As an example, a stimulus may be provided to the patient that comprises a picture of a dog and a question of the form, "Do you like dogs?" The patient may then provide a response of the form, "You don't like dogs." This may then be identified as an incorrect use of the pronoun "you" and may be further attributed to a condition such as Echolalia, where a patient repeats words without accounting for their meaning. The system may then generate a reply to the patient of the form, "I like dogs, but I can see that you don't like them." The system may place emphasis on the corrected words in order to encourage the patient to identify the correct use of the words.

As a further example, the patient may once again be presented with a stimulus that comprises a picture of a dog and a question of the form, "Do you like dogs?" The patient may provide a response of the form, "No, I don't like wolves." Analyzing the semantic components of the patient's response may allow the connection between wolves and dogs to be recognized in order to assign a level of correctness to the patient's response. In turn, a reply to the patient may be generated of the form, "I don't like wolves either, but I do like dogs." In this way, the difference may be highlighted to the patient in order to encourage the patient to correct the mistake.

In an exemplary embodiment, when a patient response is identified as correcting a previously made mistake, the response may be identified as having corrected the condition of the patient, which may then be taken forward in further conversations with the patient in order to continually monitor the patient's progression and development.

In some embodiments, a motor response of the patient to the stimulus may also be obtained. Motor response data may then be generated by analyzing the motor response, which may then be formed into a motor response vector. The motor response vector may then be combined with the original response vector of the patient in order to form an overall response vector for the patient.

In order to analyze the motor response of the patient, Video-to-Image analysis may be used to perform specific motor feature extraction and identification for specific conditions. For example, it may be possible to detect a tendency to look in a certain direction. Through the use of time stamps a motor feature may be correlated with the acoustic features of the verbal response and the linguistic features of the textual response.

For example, a tendency to squint, aligned with a modulation in the pitch of a patient's voice and the incorrect use of a pronoun, may indicate that the patient is struggling to acquire and/or form the correct response to the stimulus. In this way, a more accurate cognitive profile may be developed for the patient in the form of the overall response vector.

Figure 4:
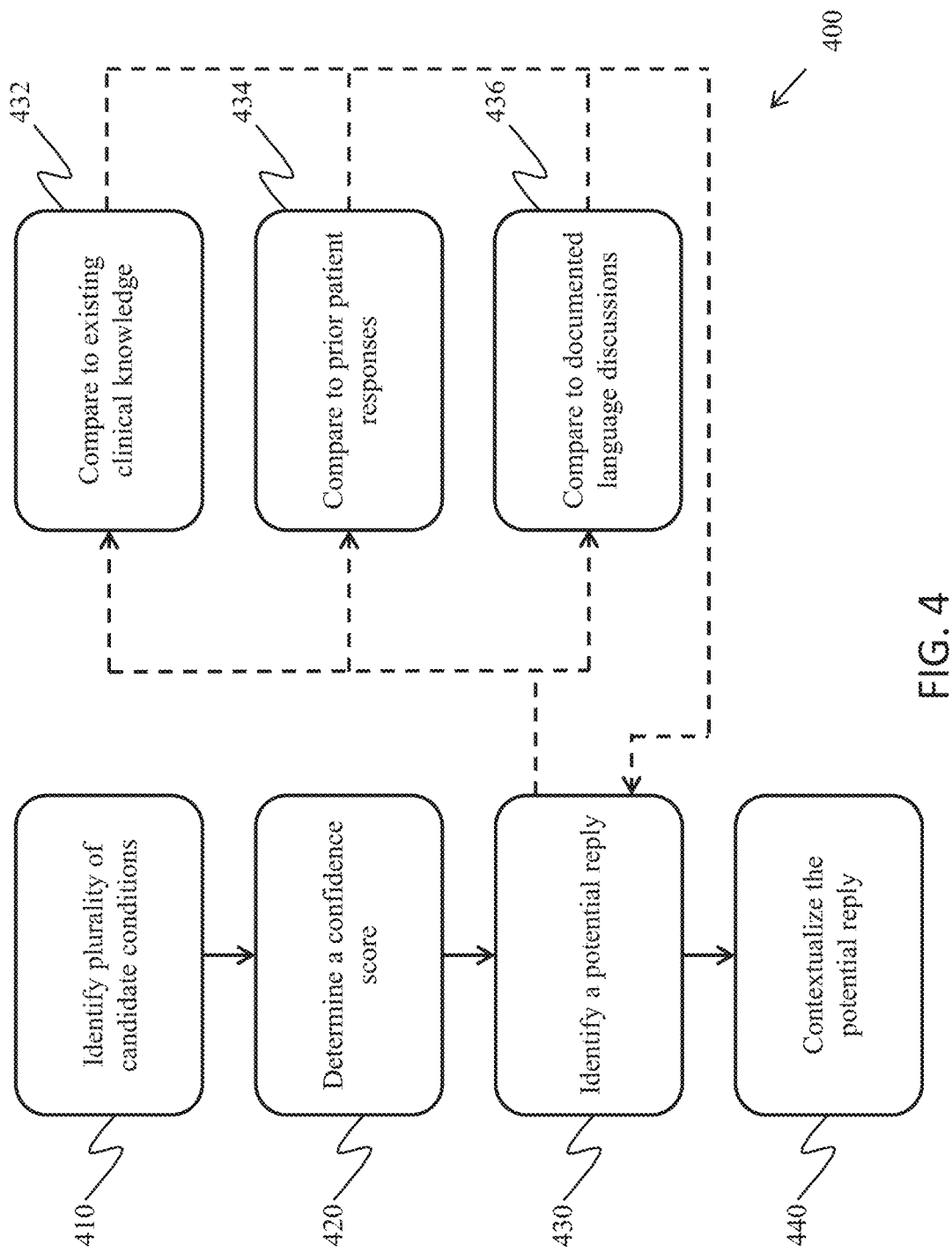
FIG. 4 depicts a flowchart of a method for determining a reply to the patient, in accordance with embodiments of the present invention.

FIG. 4 depicts a flowchart of a method 400 for determining a reply to the patient, in accordance with embodiments of the present invention. The process may begin in step 410, wherein a plurality of candidate conditions may be identified for the patient based on the analysis of the response vector.

Returning to step 350 in FIG. 3, the response vector may be classified using machine learning classifiers. The classification of the response vector may take the form of condition classification. The machine learning techniques require training sets of pre-labeled examples that may be used to train the system to create an idealized class member vector. In other words, idealized class member vectors, for each potential condition related to the use of language of a patient, may be used to allow the quick recognition of potential patient conditions. Patient conditions may be identified by comparing the patient response vector to the class member vectors. Response data from patients may also be used to enrich the class member vectors over time.

In this way, it may be possible to identify a plurality of candidate conditions for the patient by comparing the patient response vector to the class member vectors related to conditions known by the system. The candidate conditions may be identified as those that possess a class member vectors that contains similar features to the patient response vector.

In step 420, a confidence score for each candidate condition may be determined based on the contents of the response vector.

For example, the patient response vector may be compared to a class member vector using a measure such as the cosine distance. The cosine distance is a metric on the angle between the patient response vector and the class member vector. In other words, the cosine distance may be used as a measure of how closely the two vectors match. In this case, the inverse of the cosine distance may form the confidence score.

By way of example, a simple patient response vector may include one prosodic feature, the variance in pause length, one basic linguistic feature, the sentence length, and one higher level feature, the ratio of the number of grammatical errors related to pronoun use to the number of pronouns in the response. The patient response vector may take the form of [32.5, 5, 1], which may indicate a 32.5% variance in pause length, a five-word response and that every pronoun used in the response was grammatically incorrect. In this way, conditions that are associated with sporadic pause length, short sentences and incorrect pronoun usage may be identified as candidate conditions and assigned a confidence score based on how closely the response vector matches the class member vector of each candidate condition.

In some embodiments, a candidate condition may be identified as a primary condition if the associated confidence score is above a predetermined level. In other words, if the response vector of the patient is a close enough to the class member vector associated with a candidate condition, that patient may be identified as belonging to that class.

In step 430, a potential reply to the patient may be identified based on the confidence scores determined for each candidate condition in step 420.

The conversation with the patient may take the form of a graph. Each patient response and potential reply to the patient may take the form of nodes on the conversation graph. These nodes may be linked by vertices.

For example, a patient response may be obtained and indicated as a node on the conversation graph. Based on the response vector of the patient response, candidate conditions for the patient are identified, each with an associated confidence score. Based on the candidate conditions, several potential replies to the patient may be identified, appearing as subsequent nodes on the conversation graph. These potential replies may then be ranked based on the confidence score of the candidate condition associated with the reply. The potential reply with the highest rank is selected and a vertex appears between the patient response and this potential reply. The rank of the potential replies may also take into account the reply best suited to the context of the conversation with the patient and/or the previous patient response, which may be repeated across the course of a conversation.

In this way, the patient response may be compared to previous patient responses to standardized tests in order to quickly establish basic information about the patient.

The potential replies to the patient may be first identified in a number of ways. In step 432, the patient response may be compared to existing clinical knowledge, which may include standardized tests used to determine the condition of a patient that may be pre-processed by the system before interaction with a patient.

For example, a standardized test may comprise using a specific combination of stimuli that are known to produce a certain patient response in patients with a certain condition. In this way, a patient suspected of having a certain condition may be efficiently tested and assessed, rather than the system starting with no information on the patient and having to determine the potential condition over the course of a potentially long conversation. Due to the complex nature of many cognitive conditions, there may not be a single test that is capable of establishing condition identification for a patient; however, a standardized test may be employed as a method of gaining basic information about a patient. In this way, it may be possible to select a stimulus or a reply to the patient that is deemed to be the most effective for the patient, based on this basic information.

In step 434, the patient response may be compared to prior responses given by the patient. This information may be ingested by the system during a conversation with the patient, or other patients, in order to then compare the patient response with similar prior patient responses. In this way, it may be possible to identify potential replies to the patient that maintain the context of the conversation with the patient. In addition, conditions may only become evident over multiple patient responses meaning that further candidate conditions may be identified from a group of patient response that may have otherwise been overlooked.

In step 436, the patient response may be compared with documented language discussions. The documented language discussions may take the form of scientific journals, research articles, blogs, forum posts and the like. By way of example, analysis of the forum text may be performed to identify sentiment, or in other words, to identify whether the sentiment in the text is positive negative or neutral, which may then be used as an indicator of the usefulness of the text.

The text may also be processed to identify "conversation snippets", by finding quotations, identifying the relationships between quotations and assigning an "agent" to them. The resulting conversation snippets may have 'patient response' or 'reply to patient' roles associated with the quoted text, which may then be placed in a conversation database and indexed. Further annotation of the conversation may be performed using metadata relating to potential conditions. For example, this may be where a parent or care giver is asking questions or adding a comment speculating on whether the dialogue represents a specific condition. For example, there may be mention of "Echolalia" as a potential condition. Although this may not be definitive the system may capture this as additional feature metadata for the patient response to be analyzed and confirmed or refuted by the comparison of the patient response vector with the class member vector of the speculated condition.

It may be possible for a combination of steps 432, 434 and 436 to be used in order to build a profile for potential conditions beyond the training sets initially used, which may lead to a more accurate class member vector due to the increased sample size of the data and may further highlight previously unknown attributes associated with various conditions.

In step 440, the potential reply identified in step 430 is contextualized base on at least one of the previous replies to the patient, the previous patient responses and the stimulus.

Contextualization may include performing co-reference resolution across multiple patient responses in order to ensure that the subject matter of the conversation with the patient remains consistent.

Figure 5:
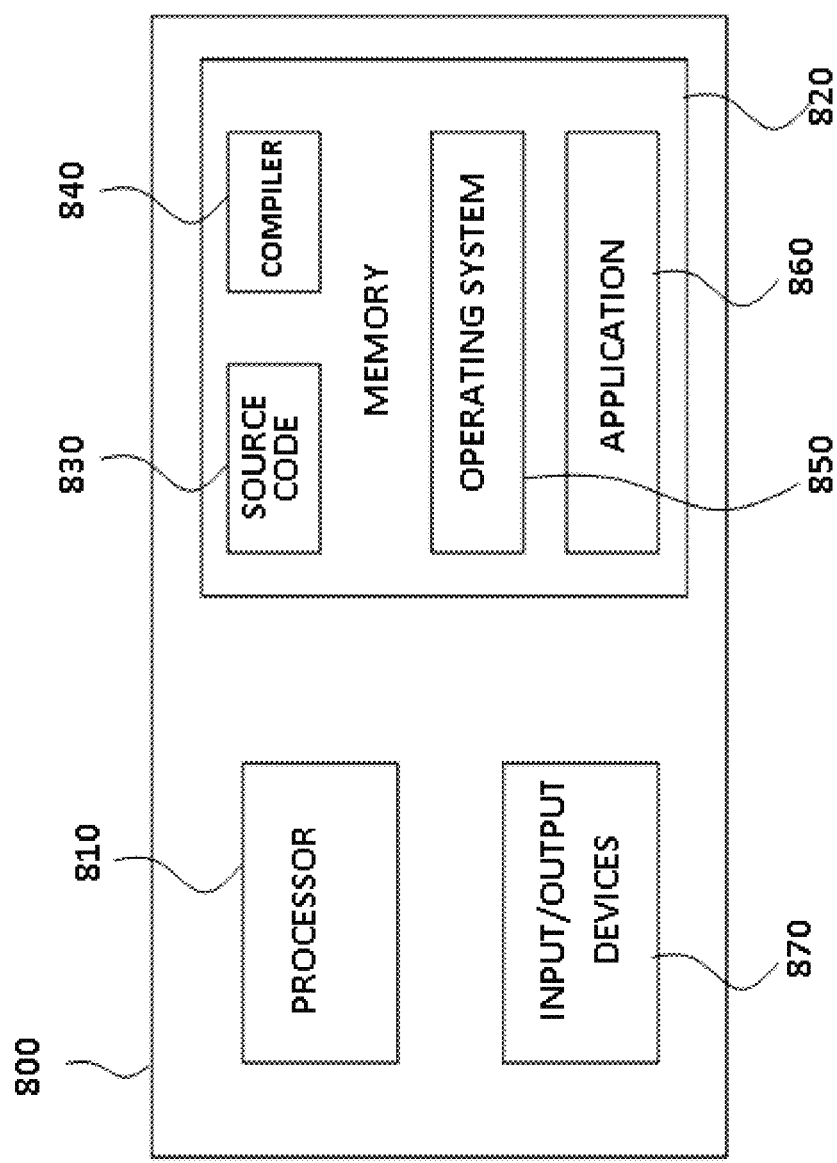
FIG. 5 depicts a block diagram of a computing system capable of implementing the data processing system of FIG. 1, and methods of FIGS. 3-4, in accordance with embodiments of the present invention.

FIG. 5 depicts a block diagram of a computing system 800 capable of implementing the data processing system of FIG. 1, and methods of FIGS. 3-4, in accordance with embodiments of the present invention. Various operations discussed above may utilize the capabilities of the computer 800. For example, one or more parts of a system for generating textual response data by analyzing the response text may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and non-volatile memory elements e.g. ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. The application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

In the context of the present application, where embodiments of the present invention constitute a method, it should be understood that such a method is a process for execution by a computer, i.e. is a computer-implementable method. The various steps of the method therefore reflect various parts of a computer program, e.g. various parts of one or more algorithms.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a storage class memory (SCM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In one embodiment, the system of the present invention may be or include a hardware device such as a computer, portable device, etc. In one embodiment, the hardware device is or includes a special-purpose device (e.g., computer, machine, portable device) that comprises specialized, non-generic hardware and circuitry (i.e., specialized discrete non-generic analog, digital, and logic based circuitry) for (independently or in combination) particularized for executing only methods of the present invention. The specialized discrete non-generic analog, digital, and logic based circuitry may include proprietary specially designed components (e.g., a specialized integrated circuit, such as for example an Application Specific Integrated Circuit (ASIC), designed for only implementing methods of the present invention).

A computer program product of the present invention may include one or more computer readable hardware storage devices having computer readable program code stored therein, said program code containing instructions executable by one or more processors of a computing system (or computer system) to implement the methods of the present invention.

A computer system of the present invention may include one or more processors, one or more memories, and one or more computer readable hardware storage devices, said one or more hardware storage devices containing program code executable by the one or more processors via the one or more memories to implement the methods of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

What is claimed is:

1. A method for monitoring a use of language of a patient, the method comprising:
   obtaining, by a processor of a computing system, a verbal response of the patient to a stimulus, the verbal response being captured as an audio file;
   storing, by the processor, the audio file in an audio format;
   converting, by the processor, the verbal response into a response text using a speech-to-text system, wherein the speech-to-text system converts the audio format to a text-based format and stores the verbal response in both the audio format and the text-based format;
   first analyzing, by the processor, a phonetic component of the verbal response by analyzing the audio file to generate verbal response data;
   second analyzing, by the processor, at least one of a semantic component and a grammatical component of the response text by performing a textual analysis of the response text to generate textual response data;
   training, by the processor, the computing system using machine learning techniques to create an idealized class member;
   classifying, by the processor, the response for each potential condition related to the use of language of the patient, wherein patient conditions are identified by comparing the response to the idealized class member;
   third analyzing, by the processor, a motor response of the patient captured by video using a video-to-image analysis to extract and identify specific motor features for specific conditions, wherein a motor feature of the patient is correlated with acoustic features of the verbal response and linguistic features of the response text;

combining, by the processor, the response and the motor response to form an overall response; and replying, by the processor, to the patient with a reply that is determined based on the overall response, eliciting further verbal responses from the patient, wherein the further verbal responses are used to enrich the idealized class member over time.

2. The method of claim 1, wherein the stimulus is selected from the group consisting of: an audible component; a visual component; a hepatic component; a taste component; a smell component; a text-based component; a question; a picture; and a video.

3. The method of claim 1, wherein the phonetic component of the verbal response comprises a pitch level.

4. The method of claim 1, wherein the step of forming a reply to the patient comprises:
identifying, by the processor, a plurality of candidate conditions by analyzing the verbal response data and the textual response data;
determining, by the processor, a confidence score for each candidate condition based on the contents of the verbal response data and the textual response data;
identifying, by the processor, a potential reply to the verbal response based on the confidence scores; and
contextualizing, by the processor, the potential reply based on at least one of the previous replies to the patient, the previous recorded verbal responses and the stimulus.

5. The method of claim 4, wherein a candidate condition is identified as a primary condition if a determined confidence score of the candidate condition is above a predetermined value.

6. The method of claim 4, wherein the step of identifying the potential reply comprises:
comparing, by the processor, the verbal response to existing clinical knowledge;
comparing, by the processor, the verbal response to prior responses given by the patient;
comparing, by the processor, the verbal response to documented language discussions; or
any combination thereof; and
identifying, by the processor, a potential reply to the patient based on the comparison.

7. A computer program product, comprising a computer readable hardware storage device storing a computer readable program code, the computer readable program code comprising an algorithm that when executed by a computer processor of a computing system implements a method for monitoring a use of language of a patient, the method comprising:
obtaining, by a processor of a computing system, a verbal response of the patient to a stimulus, the verbal response being captured as an audio file;
storing, by the processor, the audio file in an audio format;
converting, by the processor, the verbal response into a response text using a speech-to-text system, wherein the speech-to-text system converts the audio format to a text-based format and stores the verbal response in both the audio format and the text-based format;
first analyzing, by the processor, a phonetic component of the verbal response by analyzing the audio file to generate verbal response data;
second analyzing, by the processor, at least one of a semantic component and a grammatical component of the response text by performing a textual analysis of the response text to generate textual response data;
training, by the processor, the computing system using machine learning techniques to create an idealized class member;
classifying, by the processor, the response for each potential condition related to the use of language of the patient, wherein patient conditions are identified by comparing the response to the idealized class member;
third analyzing, by the processor, a motor response of the patient captured by video using a video-to-image analysis to extract and identify specific motor features for specific conditions, wherein a motor feature of the patient is correlated with acoustic features of the verbal response and linguistic features of the response text;
combining, by the processor, the response and the motor response to form an overall response; and
replying, by the processor, to the patient with a reply that is determined based on the overall response, eliciting further verbal responses from the patient, wherein the further verbal responses are used to enrich the idealized class member over time.

8. The computer program product of claim 7, wherein the phonetic component comprises a pitch level.

9. A processing system comprising at least one processor and the computer program product of claim 7, wherein the at least one processor is configured to execute the computer program code of the computer program product.

10. A computer system comprising:
a processor;
a memory device coupled to the processor; and
a computer readable storage device coupled to the processor, wherein the storage device contains program code executable by the processor via the memory device to implement a method for monitoring a use of language by a patient, the method comprising:
obtaining, by a processor of a computing system, a verbal response of the patient to a stimulus, the verbal response being captured as an audio file;
storing, by the processor, the audio file in an audio format;
converting, by the processor, the verbal response into a response text using a speech-to-text system, wherein the speech-to-text system converts the audio format to a text-based format and stores the verbal response in both the audio format and the text-based format;
first analyzing, by the processor, a phonetic component of the verbal response by analyzing the audio file to generate verbal response data;
second analyzing, by the processor, at least one of a semantic component and a grammatical component of the response text by performing a textual analysis of the response text to generate textual response data;
training, by the processor, the computing system using machine learning techniques to create an idealized class member;
classifying, by the processor, the response for each potential condition related to the use of language of the patient, wherein patient conditions are identified by comparing the response to the idealized class member;
third analyzing, by the processor, a motor response of the patient captured by video using a video-to-image analysis to extract and identify specific motor features for specific conditions, wherein a motor feature of the patient is correlated with acoustic features of the verbal response and linguistic features of the response text;
combining, by the processor, the response and the motor response to form an overall response; and
replying, by the processor, to the patient with a reply that is determined based on the overall response, eliciting further verbal responses from the patient, wherein the further verbal responses are used to enrich the idealized class member over time.

11. The computer system of claim 10, wherein the stimulus is selected from the group consisting of: an audible component; a visual component; a hepatic component; a taste component; a smell component; a text-based component; a question; a picture; and a video.

12. The computer system of claim 10, further comprising a first data generation unit is configured to generate the verbal response data, further wherein the phonetic component comprises a pitch level.

13. The computer system of claim 10, further comprising a second data generation unit is configured to generate the textual response data.

14. The computer system of claim 10, further comprising a reply generation unit configured to:
 identify a plurality of candidate conditions by analyzing the verbal response data and the textual response data;
 determine a confidence score for each candidate condition based on the contents of the verbal response data and the textual response data;
 identify a potential reply to the verbal response based on the confidence scores; and
 contextualize the potential reply based on at least one of the previous replies to the patient, the previous recorded verbal responses and the stimulus.

15. The computer system of claim 14, wherein the reply generation unit is further configured to identify a candidate condition as a primary condition if a determined confidence score of the candidate condition is above a predetermined value.

16. The computer system of claim 14, wherein the reply generation unit is, for the process of identifying a potential reply, configured to:
 compare the verbal response to existing clinical knowledge;
 compare the verbal response to prior responses given by the patient;
 compare the verbal response to documented language discussions; or
 any combination thereof; and
 identify a potential reply to the patient based on the comparison.

* * * * *